United States Patent [19]

Cope

[11] Patent Number: 5,011,478

[45] Date of Patent: Apr. 30, 1991

[54] RECESSED DILATOR-SHEATH ASSEMBLY AND METHOD

[75] Inventor: Constantin Cope, Elkins Park, Pa.

[73] Assignee: Cook Incorporation, Bloomington, Ind.

[21] Appl. No.: 304,667

[22] Filed: Jan. 31, 1989

[51] Int. Cl.⁵ .............................................. A61M 5/00
[52] U.S. Cl. .................................. 604/165; 604/264; 604/170
[58] Field of Search ............... 604/170, 171, 164, 165, 604/264, 280, 282

[56] References Cited

U.S. PATENT DOCUMENTS

| | | |
|---|---|---|
| 3,030,953 | 4/1962 | Koehn . |
| 3,082,769 | 3/1963 | Palmer . |
| 3,308,819 | 3/1967 | Arp . |
| 3,388,703 | 6/1968 | Bowes . |
| 3,459,184 | 8/1969 | Ring . |
| 3,612,050 | 10/1971 | Sheridan . |
| 4,250,881 | 2/1981 | Smith . |
| 4,502,482 | 3/1985 | DeLuccia . |
| 4,610,671 | 9/1986 | Luther . |
| 4,629,450 | 12/1986 | Suzuki et al. ........................ 128/343 |
| 4,668,221 | 5/1987 | Luther . |

FOREIGN PATENT DOCUMENTS 2811278 9/1979 Fed. Rep. of Germany .

Primary Examiner—Stephen C. Pellegrino
Attorney, Agent, or Firm—Woodard, Emhardt, Naughton, Moriarty & McNett

[57] ABSTRACT

An introducer set including a sheath and dilator is formed within a heated mold to form a smooth external shape on the set. The distal end of the sheath is embedded in the dilator and also formed at an angle oblique to the longitudinal axis of the introducer set. This construction permits the sheath to be inserted into the body with a minimum of trauma to the patient and also permits easy removal of the sheath from the dilator.

6 Claims, 2 Drawing Sheets

RECESSED DILATOR-SHEATH ASSEMBLY AND METHOD

BACKGROUND OF THE INVENTION

1. Field of the Invention

This invention relates generally to a cannula used as an aid for insertion of catheters and other instruments into the body and more particularly to a cannula which is embedded on or near the distal end of a dilator and to a method for making dilator-sheath assembly.

2. Brief Description of the Background

It is a frequent practice when introducing ballon, electrode, closed end, and other catheters or instruments into the body, to first introduce a cannula or sheath to aid in the introduction of the catheter or other instruments. Frequently the cannula or sheath will be placed on a dilator which is used on a wire guide to dilate a puncture made by a needle. It is desirable when inserting the dilator that the dilator's outside surface be as smooth as possible in order to prevent patient discomfort. To make insertion of the cannula or sheath as atraumatic as possible, it is also important that the transition between the dilator and the cannula or sheath be as even as possible.

The current design of introducer systems includes a dilator, or dummy catheter, which is surrounded by the sheath. The sheath is frequently made of thin walled Teflon, although other materials may be used. Typically, the distal end of the sheath is tapered and fitted to the dilator. However, the fit of the sheath onto the dilator does not always create a transition which is smooth enough so that the dilator and sheath will pass easily through the tissue.

Therefore, whenever fibrous tissue is encountered during the introduction of the sheath dilator combination, some resistance is encountered when the transition between the dilator and sheath is advanced through the tissue. In some cases, the distal end of the sheath is damaged during advancement through fibrous tissue. As advancement continues, the deformed sheath tip becomes harder to advance because of tearing and flaring, damaging the tissue and creating more trauma to the patient.

The present invention provides a dilator to sheath transition which is smooth, thus preventing undue trauma upon insertion into the patient.

SUMMARY OF THE INVENTION

One embodiment of the dilator-sheath assembly of the present invention is a cannula with its distal tip recessed into a dilator to prevent trauma upon insertion in patients. Because the transition between the dilator and the cannula is smooth due to the recess, little resistance is encountered when inserting the cannula. Moreover, if the recessed distal end is formed at an angle oblique to the axis of the cannula, the cannula may be easily freed from the dilator by twisting the cannula about the dilator.

One embodiment of the method of making the dilator-sheath assembly of the present invention might include heating a mold to a temperature sufficient to form a dilator-sheath assembly and forcing the dilator-sheath assembly against the mold to form it.

It is an object of the present invention to provide an improved dilator-sheath assembly which causes little trauma upon insertion into the body.

It is another object to provide a dilator-sheath assembly wherein the dilator is easily removed from the sheath.

It is a further object to provide a method for making the dilator-sheath assembly described above.

Further objects and advantages will become apparent from the following description.

DESCRIPTION OF THE PREFERRED EMBODIMENT

Figure 1:
FIG. 1 is a side view of a catheter introducer made in accordance with the prior art.

For the purpose of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

A prior art catheter introducer set is shown in FIG. 1. The structure is commercially available, one example being a Desilets-Hoffman introducer set available from Cook Incorporated of Bloomington, Indiana, under the designation TSSN or VSSN. One important feature of such a structure is the interlocking feature of the sheath and dilator which is provided by the Luer lock connection of the sheath and dilator. The interlocking feature insures that the sheath and dilator are fixed relative to one another during insertion.

Figure 2:
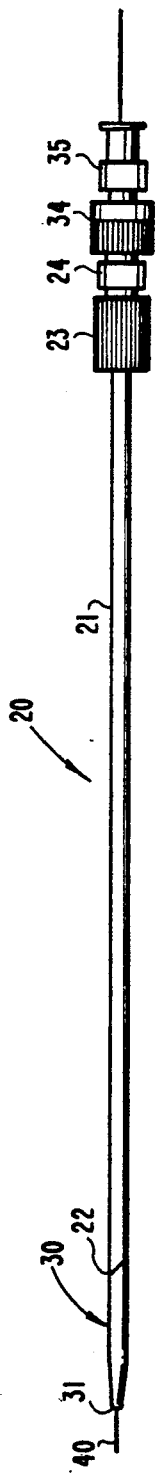
FIG. 2 is a side view of the dilator-sheath assembly of the present invention.

Referring in particular of FIG. 2, there is illustrated a dilator-sheath assembly 20 formed according to the preferred embodiment of the present invention. A cannula or sheath 21 is disposed coaxially about the dilator 30, which is in turn disposed coaxially about a wire guide 40. A portion of the dilator 30 extends distally beyond the distal end 22 of the sheath 21. The dilator's distal end 31 is tapered for enlarging the puncture site to accommodate the sheath. At the transition 22, the dilator's external diameter changes so that proximal to the transition 22, the dilator's external diameter is smaller than the external diameter distal to transition 22. With the exceptions noted, the dilator 30 is tubular and of approximately uniform internal and external diameter, having smooth external and internal surfaces, 32 and 33 respectively. The sheath 21 is also of approximately uniform thickness and diameter except at its distal end 22 where there is an external taper. The sheath is also snug about the dilator 30. At its proximal end, the sheath 21 is terminated in a cap 23 having a male Luer lock connector 24. Proximally, the dilator 30 terminates in a cap 34. The cap 34 includes a female Luer lock connector which accepts the male Luer lock connector 24. The proxilmal termination of cap 34 is a male Luer Lock connector 35. The connecting of the male Luer Lock connector 35 and the female Luer lock of the cap 34 interlocks the sheath 21 and dilator 30.

Figure 3:
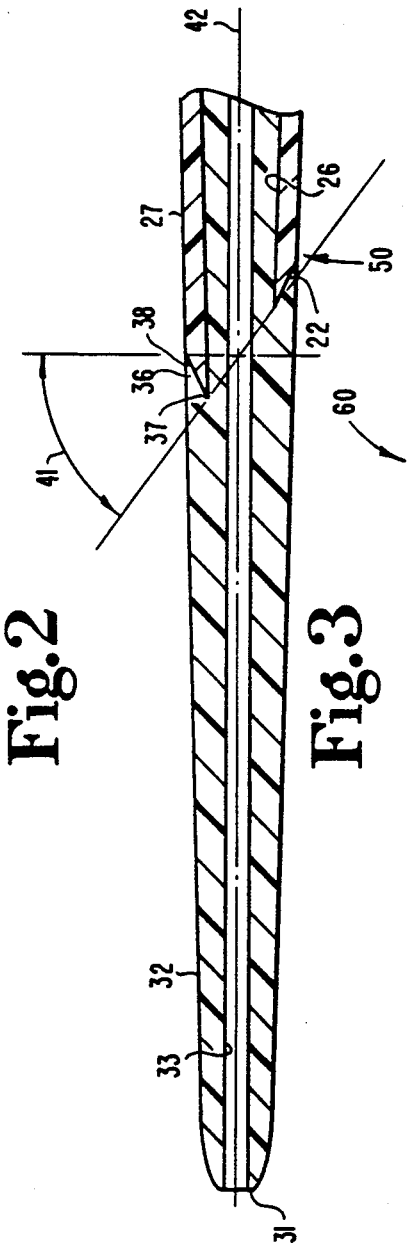
FIG. 3 is a an enlarged fragmentary cross-sectional view of the structure of FIG. 2.

FIG. 3 is an enlarged fragmentary cross-section taken along the longitudinal axis of the dilator-sheath assembly 20 and showing the distal end of the assembly 20 in detail. The wire guide 40 is shown removed. The dilator 30 is shown extending distally of the distal end 22 of the sheath 21. In general, the dilator 30 extends distally of the sheath for about 2 cm., more or less. Such extension is required to provide enough distance between the distal end 31 of the dilator 30 and the transition 50 to the sheath 21 so that a smooth taper is gradually made from the distal end 31 of the dilator 30 to the transition 50.

Throughout the length of the tubular sheath 21 it is disposed coaxially with the tubular dilator 30. Such length is approximately 16 cm, more or less, as the application requires. The inner diameter of the sheath 21 is such that its inner surfaces 26 is closely against the outer surface 32 of the dilator 30 without being so tight as to prevent movement of the sheath on the dilator. Thus, in one specific embodiment of the invention for a major portion of the length of the sheath 21 the I.D. is 0.95"±0.001" and the O.D. of the dilator 30 is 0.092"±0.002". The outer diameter of the dilator 30 increases near the tip 22 of the sheath, cutting back toward the distal end to create a spur or overlap 36 under which the distal end 22 of the sheath 21 is received. As a result of this recess 37 and the distal end 22 of the sheath 21 being received therein, a smooth transition 50 from the dilator 30 to the sheath 21 is created which eases patient stress upon insertion. Moreover, the external surface 32 of the dilator is completely even with the external surface 27 of the sheath so that the transition provides a continuous surface from external surface 32 to external surface 27. There are no edges exposed to catch on fibrous tissue.

The tip 22 of the sheath 21 as well as the recess 37 are formed at an angle 41 which is oblique to the longitudinal axis 42 of the dilator-sheath assembly 20. The most proximal edge 38 of the spur 36 is also formed at an angle oblique to the longitudinal axis. These oblique angles of the spur 36 and the distal sheath tip 22 are arranged in such a way that the embedded end 22 of the sheath 21 and the recess 37 form two coinciding ellipses. The tubular structure 21 can be easily freed from the dilator 30 by first rotating the dilator 30 relative to the sheath about the axis 42 and then withdrawing the dilator 30 from the sheath.

Figure 4:
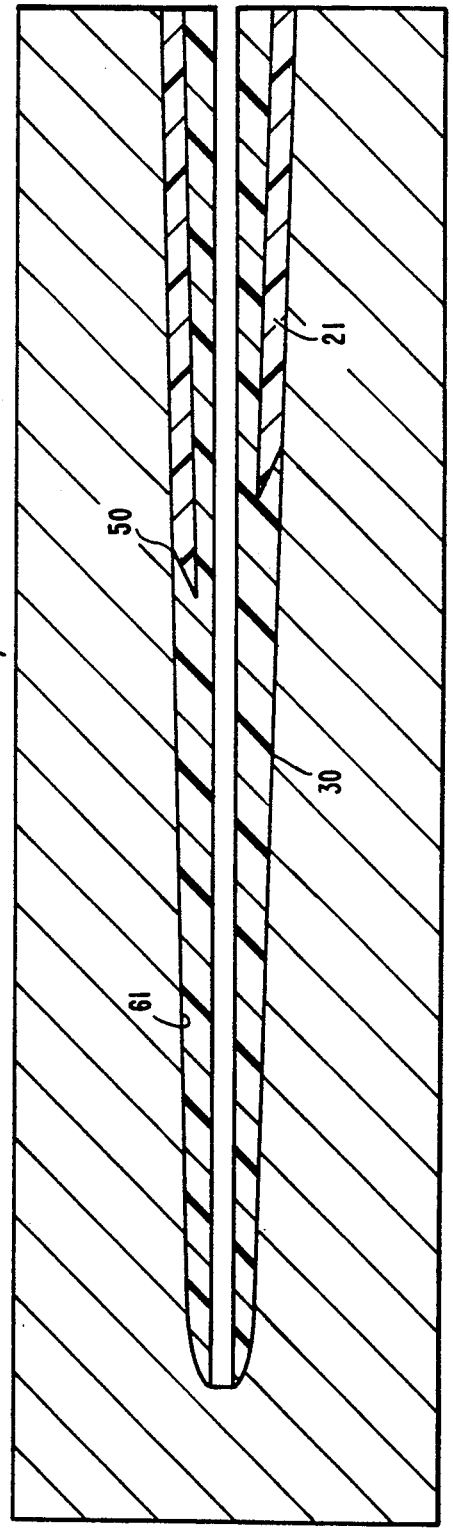
FIG. 4 is a cross-sectional view of a mold appropriate for use in forming the dilator-sheath assembly and showing a dilator-sheath assembly inserted in the mold.

The recessed dilator-sheath assembly of the present invention may be used in conjunction with various currently available catheter introducer sets designs. For example, as shown in FIGS. 2–4 and described above, a catheter introducer set, including a sheath that is not removable or splittable, like the above mentioned Desilets-Hoffman introducer set of FIG. 1, may be formed with the recessed dilator sheath of the present invention. Alternatively, the recessed dilator sheath of the present invention may be used in a catheter introducer set having a sheath which is removable or splittable. In this alternative embodiment of the present invention, the recessed dilator sheath is used with a sheath as described, for example, in U.S. Pat. No. Re. 31,855.

The recessed dilator sheath of this invention may be used as follows. First, a percutaneous needle is inserted through the skin and body tissue into the vein or artery or other vessel to be catheterized. A wire guide 40 may then be inserted into the body and vessel through the needle. The needle is then removed from the puncture site, leaving the wire guide 40 in place. The dilator-sheath assembly 20 is then inserted into the body over the wire guide 40. As the dilator 30 is advanced into the body, the puncture hole gradually increases in diameter as a result of the distal tapering of the dilator 30. The insertion proceeds smoothly past the transition 50 between the dilator 30 and sheath 21 because the sheath's distal end 22 is embedded in the dilator 30 and cannot catch on body tissue. Twisting the dilator relative to the sheath about the axis 42 frees the sheath 21 from the recess 37, thus facilitating the removal of the dilator 30 from the body and the sheath. The sheath 21 remains in the body allowing access to the target body cavity.

Teflon (Teflon is the Dupont trademark for polytetrafluoroethylene) used in the preferred embodiment as the sheath material is virgin material, i.e., has not previously been used or reground. It is free of foreign matter and dye marks. These characteristics are required to ensure compatibility for insertion into the body.

A mold 60 as shown in FIG. 4 may be used to form the distal end of dilator-sheath assembly 20. In order to make the dilator-sheath assembly, the mold 60 is heated to a temperature at which the dilator material softens and becomes flowable. The dilator-sheath assembly 20 is inserted into the mold 60. The internal surface 61 of the mold 60 defines a space identical to the external surface of the dilator-sheath assembly 20 described by the line from surface 32 to surface 27. The recess defined by the mold's internal surface 61 is such that the dilator-sheath assembly 20 is insertable far enough within the mold 60 so that the dilator-sheath transition 50 is well within the mold 60. Because of this resultant flowability of the dilator material, the spurs 36 on the dilator form immediately next to the tapered distal end 22 of the sheath 21. The sheath 21, made of a higher melting material, typically Teflon, than the dilator 30, will not become flowable. However, it is important in this process that the mold 60 not be heated to a temperature sufficient to cause the sheath material to become softened and flowable. This is because the sheath material must remain rigid in order to partially define the boundaries to which the dilator material is free to flow. Thus, the internal surface 61 of the mold 60 defines the latitudinal boundaries while the distal end 22 of the sheath 21 defines the longitudinal boundaries of flow. As a result of the heating the dilator external surface 32 and the sheath external surface 27 are coplanar immediately proximal to the distal taper of the dilator 30. Once the desired result is achieved, i.e. the dilator material flows to form the recess 37 defined by the distal end 22 of the sheath 21, the mold and dilator-sheath assembly therein are allowed to cool, thus firmly setting the dilator material. The dilator-sheath assembly may then be removed from the mold.

While particular embodiments of the invention have been illustrated and described in detail in the drawing and foregoing description, it is to be understood that this description is made only by way of example and not as a limitation to the scope of the invention which is claimed below.

THE INVENTION CLAIMED IS:

1. A dilator-sheath assembly comprising:
a sheath having one end adapted to be inserted in the body;
a dilator within said sheath and having a distal end extending beyond the one end of the sheath, said dilator having a recess within which said one end of said sheath is received whereby said dilator shields said one end of said sheath when the dilator-sheath assembly is inserted in the body, said dilator having an annular spur extending around said dilator and contiguous to said one end of said sheath, said spur defining said recess.

2. The dilator-sheath assembly of claim 1 wherein said one end of said sheath is externally tapered.

3. A dilator-sheath assembly comprising:
a sheath having one end adapted to be inserted in the body;
a dilator within said sheath and having a distal end extending beyond the one end of the sheath, said dilator having a recess within which said one end of said sheath is received whereby said dilator shields said one end of said sheath when the dilator-sheath assembly is inserted in the body;
said sheath and dilator having longitudinal axes and being coaxial, said one end of said sheath being formed at an angle oblique to the longitudinal axis of said sheath and said dilator whereby rotation of said dilator and said sheath relative to one another about said axes disengages said one end of said sheath from said dilator recess.

4. A dilator-sheath assembly comprising:
a sheath, said sheath being compatible for insertion within the body and having one end adapted to be inserted in the body;
a dilator within said sheath and having a distal end extending beyond the one end of said sheath; and
a transition means defined by an increase in the outer diameter of said dilator such that the outer diameter of said dilator is approximately equal to the outer diameter of said sheath at the one end of said sheath; and
wherein said transition means includes a continuous annular spur disposed about said dilator so that said one end of said sheath is received under said continuous annular spur.

5. A dilator-sheath assembly comprising:
a sheath, said sheath being compatible for insertion within the body and having one end adapted to be inserted in the body;
a dilator within said sheath and having a distal end extending beyond the one end of said sheath; and
a transition means defined by an increase in the outer diameter of said dilator such that the outer diameter of said dilator is approximately equal to the outer diameter of said sheath at the one end of said sheath; and
wherein said one end of said sheath is externally tapered.

6. A dilator-sheath assembly comprising:
a sheath formed of flexible plastic material, said sheath being compatible for insertion within the body and having one end adapted to be inserted in the body;
a dilator within said sheath and having a distal end extending beyond said one end of said sheath, said dilator being formed of flexible plastic material;
a transition means defined by an increase in the outer diameter of said dilator such that the outer diameter of said dilator is approximately equal to the outer diameter of said sheath at said one end of said sheath; and
wherein said one end of said sheath is formed to an angle oblique to the longitudinal axis of said sheath, and further in which said transition means is formed at an angle oblique to the longitudinal axis of said dilator so that said one end of said sheath is contiguous with said transition means.

* * * * *

UNITED STATES PATENT AND TRADEMARK OFFICE
CERTIFICATE OF CORRECTION

PATENT NO. : 5,011,478
DATED     : April 30, 1991
INVENTOR(S) : Constantin Cope

It is certified that error appears in the above-identified patent and that said Letters Patent is hereby corrected as shown below:

On the title page in the heading, at the area designating the Assignee, please delete "Incorporation" and insert --Incorporated--.

At column 3, line 18, delete "surfaces" and insert --surface--.

At column 3, line 23, delete "0.95" and insert --.095--.

Signed and Sealed this

Twenty-fifth Day of August, 1992

Attest:

DOUGLAS B. COMER

Attesting Officer          Acting Commissioner of Patents and Trademarks